United States Patent [19]

Ono et al.

[11] Patent Number: 4,493,846
[45] Date of Patent: Jan. 15, 1985

[54] BICYCLOOCTANE DERIVATIVES

[75] Inventors: Keiichi Ono, Osaka; Akihiko Sugie, Toyonaka; Hajime Kawakami, Takarazuka; Shunsuke Sami, Toyonaka; Atsuyuki Kojima, Takarazuka; Junki Katsube, Toyonaka, all of Japan

[73] Assignee: Sumitomo Chemical Company, Limited, Osaka, Japan

[21] Appl. No.: 243,570

[22] Filed: Mar. 13, 1981

[30] Foreign Application Priority Data

Mar. 21, 1980 [JP] Japan .................... 55/36720
Jul. 8, 1980 [JP] Japan .................... 55/93664

[51] Int. Cl.$^3$ .................. C07C 69/608; C07C 69/616; C07C 61/13; C07C 61/28
[52] U.S. Cl. .................. 424/308; 424/305; 424/317; 260/464; 260/465 D; 260/465 F; 560/56; 560/119; 562/466; 562/501; 568/633; 568/648; 568/649; 568/665; 564/172; 564/180; 564/188; 549/372; 549/453
[58] Field of Search .................. 560/56, 119; 562/466, 562/501; 424/305, 308, 317

[56] References Cited

U.S. PATENT DOCUMENTS 4,096,337 6/1978 Marsham .................. 560/56 X

FOREIGN PATENT DOCUMENTS 2017699 10/1979 United Kingdom .

OTHER PUBLICATIONS

Whittle, et al., Prostaglandins, 19, (4), pp. 605-627, (1980).
Whittle, et al., Communications, J. Pharm. Pharmacol., (1980), 32, pp. 603-604.
Moncada, et al., Nature, 263, 1976, pp. 663-665.

Primary Examiner—Joseph Paul Brust
Attorney, Agent, or Firm—Stevens, Davis, Miller & Mosher

[57] ABSTRACT

A compound of the formula

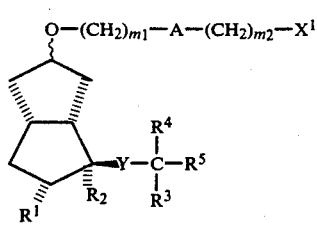

wherein $X^1$ is a free or esterified carboxyl group, a hydroxymethyl group, a cyano group, a group of the formula:

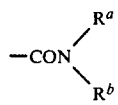

($R^a$ and $R^b$ are each independently a hydrogen atom, a $C_1$-$C_4$ alkyl group, a $C_3$-$C_7$ cycloalkyl group, a benzyl group, a phenyl group, a phenyl group substituted with a halogen atom or a $C_1$-$C_4$ alkyl group, or, when taken together with the adjacent nitrogen atom to which they are attached, they represent a 5 to 7-membered saturated heterocyclic group) or a group of the formula:

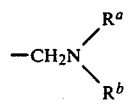

($R^a$ and $R^b$ are each as defined above), Y is an ethylene group or a vinylene group, $R^1$ is a hydrogen atom, a hydroxyl group or a protected hydroxyl group, $R^2$ is a hydrogen atom or $R_1$ and $R_2$, when taken together, means a single linkage to form a double bond between the carbon atoms which they are linked, $R^3$ is a hydroxyl group or a protected hydroxyl group, $R^4$ is a hydrogen atom or a $C_1$-$C_4$ alkyl group, $R^5$ is a hydrogen atom, a $C_3$-$C_8$ alkenyl group, a $C_3$-$C_8$ alkynyl group, a $C_1$-$C_8$ alkyl group, a $C_3$-$C_7$ cycloalkyl group or a group of the formula: —$(CH_2)_n$—B (n is 1 or 2 and B is a $C_1$-$C_4$ alkoxyl group, a $C_3$-$C_7$ cycloalkyl group, or a phenyl or phenoxy group optionally substituted with a halogen atom, a $C_1$-$C_4$ alkyl group, a trifluoromethyl group or a $C_1$-$C_4$ alkoxyl group), A is a group of either one of the formulae:

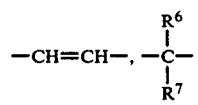

($R^6$ and $R^7$ are each independently a hydrogen atom or a $C_1$-$C_4$ alkyl group) and

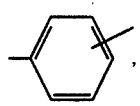

$m_1$ is 1 or 2 and $m_2$ is 0, 1 or 2, and the non-toxic pharmaceutically acceptable salts threreof. Said compounds have strong anti-ulcerogenic activity and are useful in treatment of gastraintestinal ulcer.

20 Claims, No Drawings

BICYCLOOCTANE DERIVATIVES

The present invention relates to novel bicyclooctane compounds, their production and use.

More particularly, this invention relates to novel bicyclooctane compounds, to a pharmaceutical composition containing at least one of the bicyclooctane compounds and to a process for production thereof.

The novel bicyclooctane compounds provided by the present invention are those represented by the formula [I]:

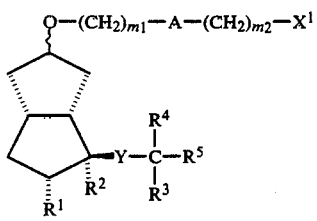

wherein $X^1$ is a free or esterified carboxyl group, a hydroxymethyl group, a cyano group, a group of the formula:

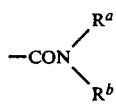

($R^a$ and $R^b$ are each independently a hydrogen atom, a $C_1$–$C_4$ alkyl group, a $C_3$–$C_7$ cycloalkyl group, a benzyl group, a phenyl group, a phenyl group substituted with a halogen atom or a $C_1$–$C_4$ alkyl group, or, when taken together with the adjacent nitrogen atom to which they are attached, represent a 5 to 7-membered saturated heterocyclic group) or a group of the formula:

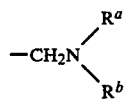

($R^a$ and $R^b$ are each as defined above), Y is an ethylene group or a vinylene group, $R^1$ is a hydrogen atom, a hydroxyl group or a protected hydroxyl group, $R^2$ is a hydrogen atom, or $R_1$ and $R_2$, when taken together, means a single linkage to form a double bond between the carbon atoms to which they are linked, $R^3$ is a hydroxy group or a protected hydroxyl group, $R^4$ is a hydrogen atom or a $C_1$–$C_4$ alkyl group, $R^5$ is a hydrogen atom, a $C_3$–$C_8$ alkenyl group, a $C_3$–$C_8$ alkynyl group, a $C_1$–$C_8$ alkyl group, a $C_3$–$C_7$ cycloalkyl group or a group of the formula: —$(CH_2)_n$—B (n is 1 or 2 and B is a $C_1$–$C_4$ alkoxyl group, a $C_3$–$C_7$ cycloalkyl group, or a phenyl or phenoxy group optionally substituted with a halogen atom, a $C_1$–$C_4$ alkyl group, a trifluoromethyl group or a $C_1$–$C_4$ alkoxyl group), A is a group of either one of the formulae:

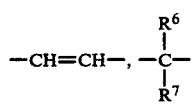

($R^6$ and $R^7$ are each independently a hydrogen atom or a $C_1$–$C_4$ alkyl group) and

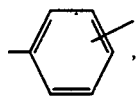

$m_1$ is 1 or 2 and $m_2$ is 0, 1 or 2.

Among the bicyclooctane compounds of the formula [I], the preferred compounds are, with respect to the formula [I], those in which $R^1$ is a hydroxy group and Y is a vinylene group.

Further more preferred compounds may be represented by the formula:

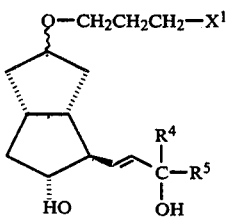

wherein $R^4$, $R^5$ and $X^1$ are each as defined above.

In the significances as used above, the term "halogen" includes fluorine, chlorine, bromine and iodine; the terms "$C_1$–$C_4$ alkyl" and "$C_1$–$C_4$ alkoxy" are each meant straight or branched chain alkyl and alkoxy groups having from 1 to 4 carbon atoms (e.g. methyl, ethyl, n-propyl, isopropyl, n-butyl, methoxy, ethoxy, n-propoxy, isopropoxy, n-butoxy, etc.).

The term "$C_1$–$C_8$ alkyl" is meant a straight or branched chain alkyl group having from 1 to 8 carbon atoms (e.g. methyl, ethyl, n-propyl, isopropyl, n-butyl, n-pentyl, isobutyl, isopentyl, 1-methylpentyl, 2-ethylpentyl, 1,1-dimethylpentyl, 2-methylpentyl, n-hexyl, 2-methylhexyl, etc.) and the terms "$C_3$–$C_8$ alkenyl" and "$C_3$–$C_8$ alkynyl" are each meant straight or branched chain alkenyl and alkynyl groups having from 3 to 8 carbon atoms (e.g. propenyl, 2-butenyl, 2-pentenyl, 2-hexenyl, 5-heptenyl, 6-methyl-hept-5-enyl, 3-pentenyl, 4-pentenyl, 2-propynyl, 2-butynyl, 2-pentynyl, 3-pentynyl, 4-pentynyl, 5-heptynyl, 6-heptynyl, etc.). The term "$C_3$–$C_7$ cycloalkyl" includes cyclopropyl, cyclobutyl, cyclohexyl, cyclopentyl, cycloheptyl. The term "esterified carboxyl group" includes $C_1$–$C_4$ alkoxycarbonyl, aryloxycarbonyl (e.g. phenoxycarbonyl, naphthoxycarbonyl), aralkyloxycarbonyl (e.g. benzyloxycarbonyl, phenetyloxycarbonyl), ($C_1$–$C_4$ alkoxy)methoxycarbonyl, ($C_2$–$C_5$ alkanoyloxy)methoxycarbonyl (e.g. acetoxymethoxycarbonyl, pivaloyloxymethoxycarbonyl), ($C_3$–$C_7$ cycloalkyloxy)carbonyl, arylcarbonylmethoxycarbonyl and (hydroxy-$C_1$–$C_4$ alkoxy)carbonyl. The term "5 to 7-membered saturated heterocyclic group" includes piperidino, pyrrolidino, homopiperidino, morpholino, piperadino, N-($C_1$–$C_4$)alkylpiperazino. The term "protected hydroxy group" is meant a hydroxy group protected with $C_1$–$C_4$ alkanoyl, benzoyl, substituted benzoyl, tetrahydropyranyl, tetrahydrofuryl or ($C_1$–$C_4$ alkoxy)alkyl.

A tremendous amount of research in synthetic organic chemistry, pharmacology and clinical medicine of prostaglandins has been performed since discovery of prostaglandins.

In 1976, J. Vane of Wellcome foundation reported isolation and biological effects of prostacyclin [prostaglandin I₂]. [S. Moncada, R. Grygłewski, S. Bunting, and J. R. Vane, Nature (London), 263, 663 (1976)].

Prostaglandin I₂ [II], which is shown below, has several excellent pharmacological activities, for example, hypotensive, vasodilating, antiallergic, antiulcerogenic, antithrombotic activity, and is expected to be useful in treating asthma, ulcer, thrombosis or hypertention.

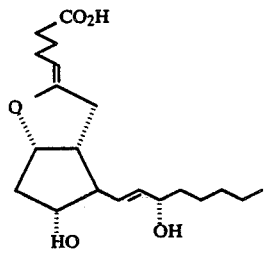

However, prostaglandin I₂ may not be used as medicine owing to its instability and variety of pharmacological actions.

As the result of a study, it has now been found that the novel bicyclooctane compounds [I] of the present invention and their non-toxic pharmaceutically acceptable salts have strong anti-ulcerogenic activity without the undesirable pharmacological actions and are useful in treatment of the gastrointestinal ulcer. In addition, the undesirable chemical instability is absent in the compounds [I] of this invention.

Accordingly, a basic object of the present invention is to provide novel and stable bicyclooctane compounds [I] having selective antiulcerogenic activity. Another object of the present invention is to provide a process for producing those compounds [I]. Further object of the present invention is to provide a pharmaceutical composition containing a compound of the formula [I]. These and other objects will be apparent to those skilled in the art to which the present invention pertains from the foregoing and subsequent descriptions.

The novel bicyclooctane compound [I] of the invention can be prepared by the following several methods.

(1) The bicyclooctane compound of the formula [I]

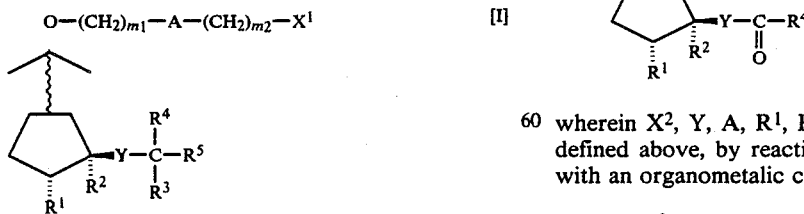

wherein $X^1$, Y, A, $R^1$, $R^2$, $R^3$, $R^4$, $R^5$, $m_1$ and $m_2$ are each as defined above, can be prepared from a carbonyl compound of the formula [III]:

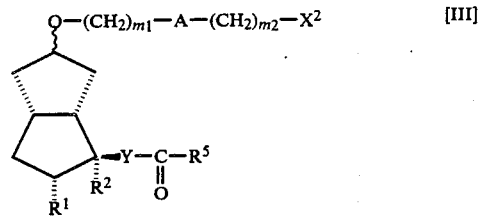

wherein $X^2$ is a free or esterified carboxyl group or a cyano group and Y, A, $R^1$, $R^2$, $R^5$, $m_1$ and $m_2$ are each as defined above by reacting the latter with a reducing agent or an organometalic compound of the formula:

$$M\text{—}R^8 \quad [IV]$$

wherein $R^8$ is a $C_1$-$C_4$ alkyl group and M is a lithium atom or —Mg halo (halo is a halogen atom), optionally followed by hydrolysis of a cyano or ester group, esterification of a carboxyl group, reduction of a free or esterified carboxyl group, amidation of a free or esterified carboxyl group, reduction of a vinylene group, protection of a hydroxyl group, deprotection of a protected hydroxyl group and/or reduction of an amide or cyano group.

(2) The bicyclooctane compounds of the formula [Ia]:

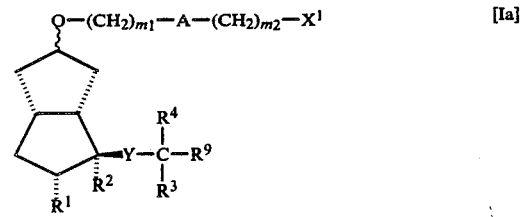

wherein $X^1$, Y, A, $R^1$, $R^2$, $R^3$, $R^4$, $m_1$ and $m_2$ are each as defined above and $R^9$ is a $C_1$-$C_8$ alkyl group, a $C_3$-$C_8$ alkenyl group, a $C_3$-$C_8$ alkynyl group, a $C_3$-$C_7$ cycloalkyl group or a group of the formula: —(CH₂)ₙ—E (n is 1 or 2, and E is a $C_3$-$C_7$ cycloalkyl group, a phenyl group optionally substituted with a halogen atom, a $C_1$-$C_4$ alkyl group, a trifluoromethyl group or a $C_1$-$C_4$ alkoxyl group), can be prepared from a carbonyl compound of the formula:

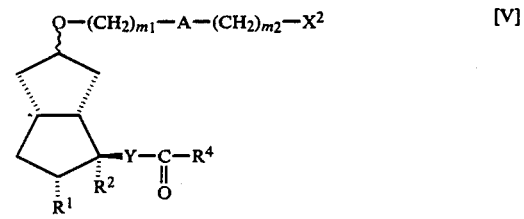

wherein $X^2$, Y, A, $R^1$, $R^2$, $R^4$, $m_1$ and $m_2$ are each as defined above, by reacting a carbonyl compound [V] with an organometalic compound of the formula:

$$M\text{—}R^9 \quad [VI]$$

wherein M and $R^9$ are each as defined above, optionally followed by hydrolysis of a cyano or ester group, esterification of carboxyl group, reduction of a free or esterified carboxyl group, amidation of a free or esterified carboxyl group, reduction of a vinylene group, protection of a hydroxyl group, deprotection of a protected hydroxyl group and/or reduction of an amide or cyano group.

(3) The bicyclooctane compound of the formula [Ib]:

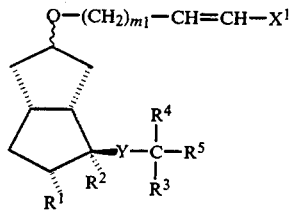

wherein $R^1$, $R^2$, $R^3$, $R^4$, $R^5$, Y, $X^1$ and $m_1$ are each as defined above, can be prepared from the alcohol of the formula [VIII]:

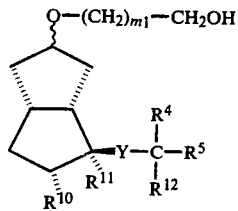

wherein $R^4$, $R^5$, $m_1$ and Y are each as defined above and $R^{10}$ is a hydrogen atom or a protected hydroxy group, $R^{11}$ is a hydrogen atom, or $R^{10}$ and $R^{11}$, when taken together, means a single linkage to form a double bond between the carbon atoms to which they are linked, and $R^{12}$ is a protected hydroxy group by reacting the latter with an oxidizing agent to give the aldehyde of the formula [VIII]:

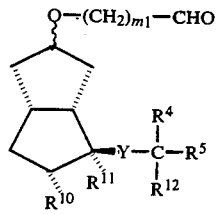

wherein $R^4$, $R^5$, $R^{10}$, $R^{11}$, $R^{12}$, $m_1$ and Y are each as defined above, followed by reacting the resulting compound with a compound of the formula:

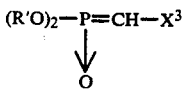

wherein $X^3$ is a cyano group or an esterified carboxyl group, and R' is a $C_1$-$C_4$ alkyl group, optionally followed by hydrolysis of a cyano or ester group, esterification of a carboxyl group, reduction of a free or esterified carboxyl group, amidation of a free or esterified carboxyl group, reduction of an amide or cyano group and/or deprotection of a protected hydroxy group.

The sequence of the steps from the carbonyl compound [III, V] or the alcohol [VIII] to the bicyclooctane compound [I, Ia, Ib] as state above may be represented by the following schema:

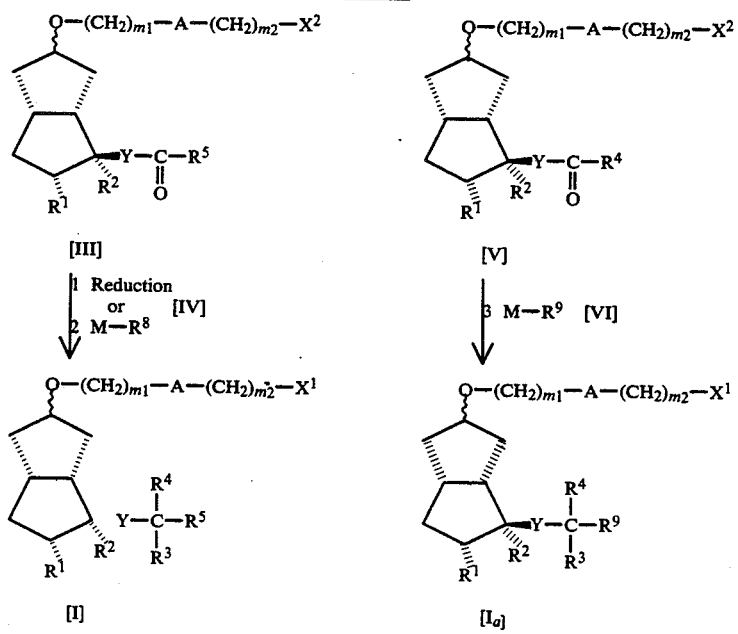

Scheme A

Scheme A

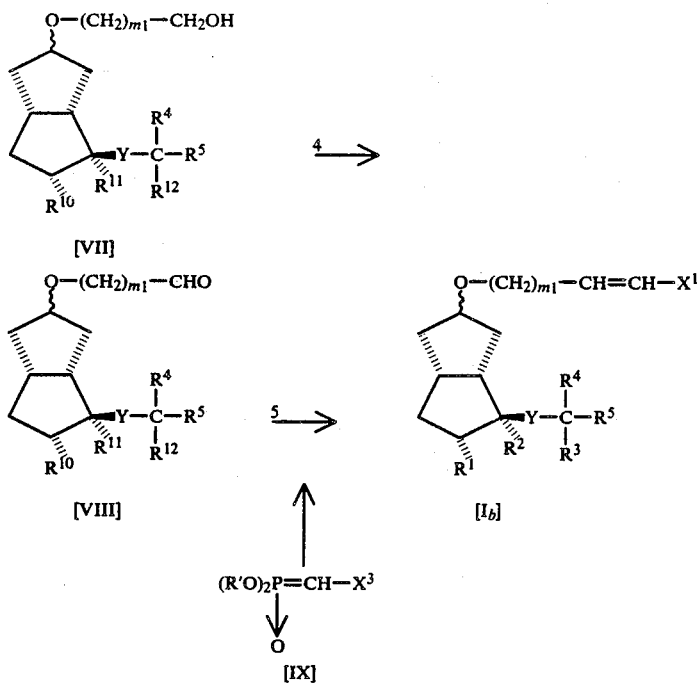

wherein $X^1$, $X^2$, $X^3$, Y, A, M, $R^1$, $R^2$, $R^3$, $R^4$, $R^5$, $R^8$, $R^9$, $R^{10}$, $R^{11}$, $R^{12}$, R', $m_1$ and $m_2$ are each as defined above.

Step-1

Production of the bicyclooctane compound [I] from the carbonyl compound [III] by reduction of a carbonyl group. The carbonyl compound [III] can be converted into the corresponding alcohol compound by reacting of the former with reducing agent in an inert solvent (e.g. THF, ether, dimethoxyethane, pentane, hexane, benzene, toluene, methanol, ethanol) at a range of the temperature from −70° C. to room temperature.

As the reducing agent, there may be used for example trialkylborohydride (e.g. lithium triisobutyl borohydride), bis(2,4,6-tri-tert-butylphenoxy)aluminum hydride, sodium borohydride, zinc borohydride, diisobutyl aluminum hydride, diisobutyl aluminum-2,6-di-t-butyl-4-methylphenol, 1,1'-binaphthyl-2,2'-dioxyaluminum lithium hydride).

The protection and deprotection of a hydroxyl group can be carried out by conventional procedure [Protective Group in Organic Chemistry, Edited by J. F. W. McOmie (1973) 95–143].

The reduction of a vinylene group can be accomplished by catalytic hydrogenation in an inert solvent (e.g. alkanol, aqueous alkanol) at a range of the temperature from 0° C. to room temperature.

Step-2 and 3

Reaction of a carbonyl compound [III, V] with an organometalic compound [IV, VI].

The carbonyl compound ([III] or [V]) can be converted into the corresponding alcohol compound by reacting the former with an organometalic compound [IV, VI] in an inert solvent (e.g. ether, THF, dioxane) at a range of the temperature from −70° C. to room temperature. The organometalic compound ([IV] or [VI]) can be prepared by the conventional procedures.

Step-4

The oxidation of an alcohol compound [VII] can be carried out by conventional procedure in the presence of a suitable oxidizing agent (e.g. Collin's reagent, Sarett reagent, piridinium chlorochromate) in an inert solvent (e.g. dichloromethane, dichloroethane, pyridine) at a range of the temperature from 0° C. to room temperature.

Step 5

The witting reaction of an aldehyde compound [VIII] can be carried out by reacting of the compound [VIII] with a wittig reagent [IX] in an inert solvent (e.g. ether, THF, dioxane, benzene, toluene, hexane, DMSO) at a range of the temperature from 0° C. to room temperature. The wittig reagent [IX] can be prepared by the conventional procedures.

The steps of amidation of a carboxyl group, amidation of a esterified carboxyl group, hydrolysis of a cyano group into a carboxyl group, reduction of cyano or amide group, hydrolysis of an esterified carboxyl group, esterification of a carboxyl group and reduction of a free or esterified carboxyl group may be represented by the following schema:

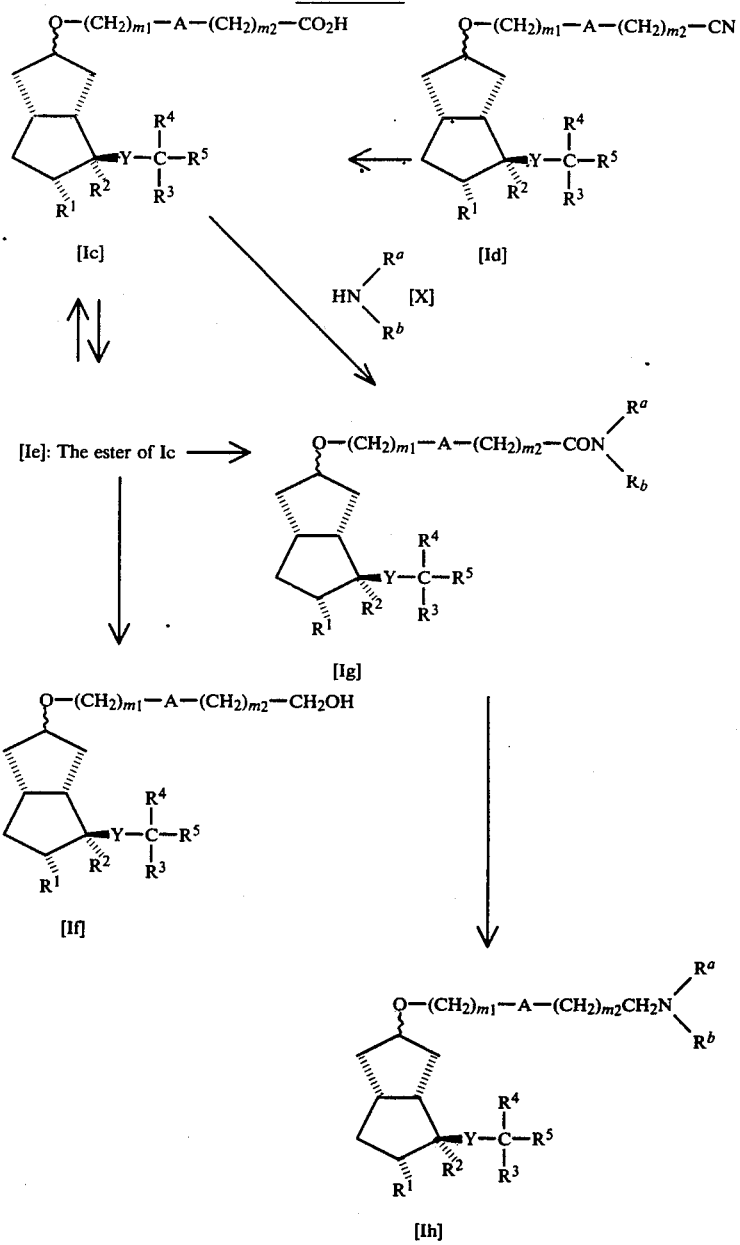

Amidation of a carboxyl group can be carried out by conventional procedure. For instance, it can be accomplished in an inert solvent (e.g. ether, THF) by treating a carboxyl compound [Ic] with an amine of the formula:

   [X]

($R^a$ and $R^b$ are each as defined above)
in the presence of dehydrolyzing agent (e.g. dicyclohexylcarbodiimide) at a range of the temperature from 0° to room temperature, or by treating the functionally active derivative (e.g. mixed acid anhydride) of [Ic] with the amine [X] in an inert solvent (e.g. ether, THF, chloroform) at a range of the temperature from −10° C. to room temperature.

Amidation of an esterified carboxyl group can be carried out by treating an ester compound [Ie] with the amine [X] in an inert solvent (e.g. DMF, methanol, ethanol, THF) at a range of the temperature from room temperature to the boiling temperature of the solvent.

Hydrolysis of a cyano group into a carboxyl group can be carried out in the presence of an alkali (e.g. sodium hydroxide, potassium hydroxide) in an inert solvent (e.g. aqueous alkanol, DMSO) at a range of the temperature from 30° C. to the boiling temperature of the solvent.

Reduction of a cyano or amide group can be carried out by treating a cyano or amide compound [Id, Ig] with the reducing agent in an inert solvent (e.g. ether, THF, dioxane, benzene, toluene) at a range of the temperature from room temperature to the boiling temperature of the solvent. Though various reducing agent may be employed in the reduction, it is especially preferable to use metal hydride compound such as lithium aluminum hydride.

The hydrolysis of an ester compound [Ie] and the esterification of a carboxyl group can be carried out by conventional procedure.

The reduction of a free or esterified carboxyl group can be also carried out by conventional procedure, for example, metal hydride reduction procedure.

The carbonyl compound [III, V] used as an intermediate in the present invention can be prepared from a ketone compound [XI] by the process shown in the scheme C, D or E.

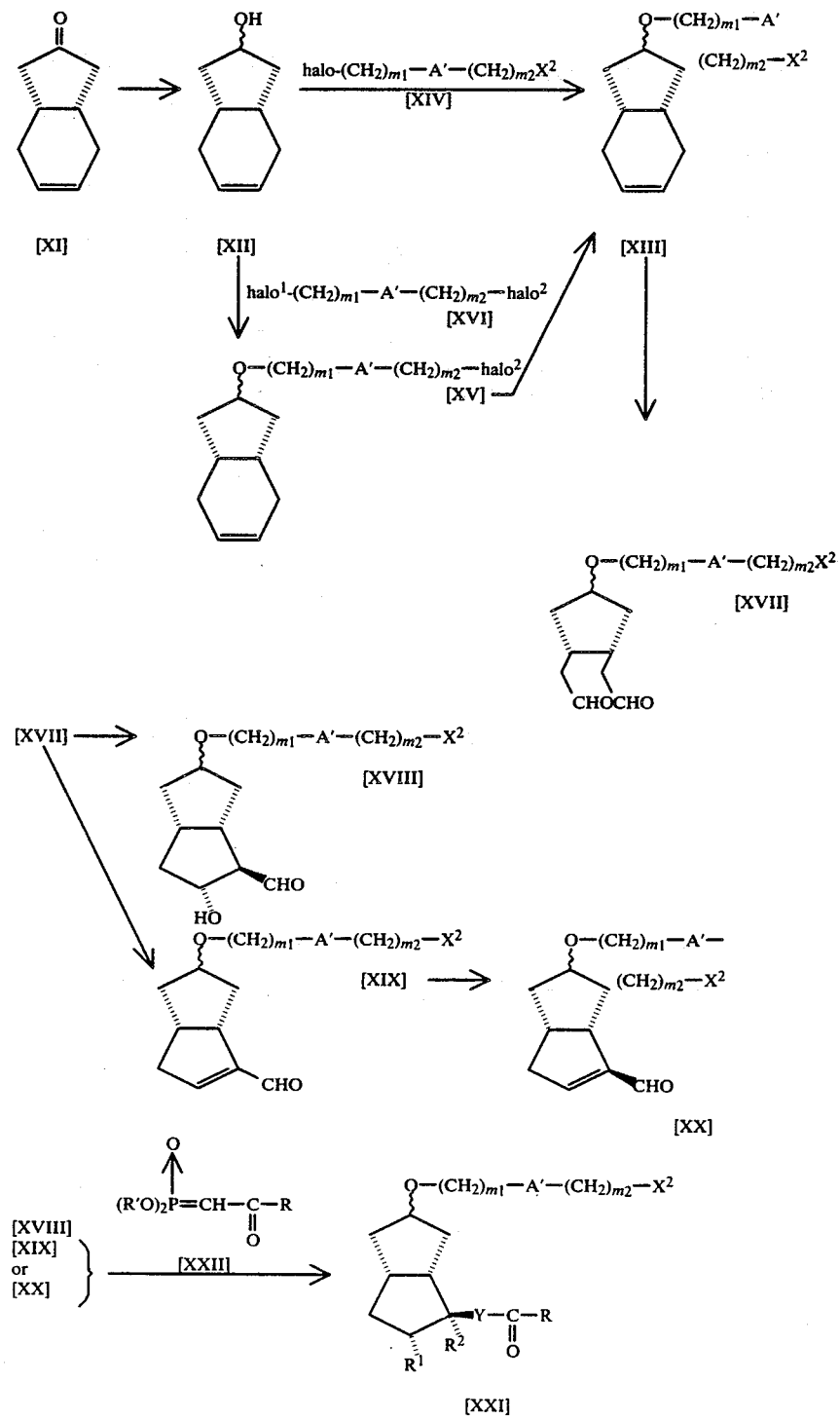

scheme-C

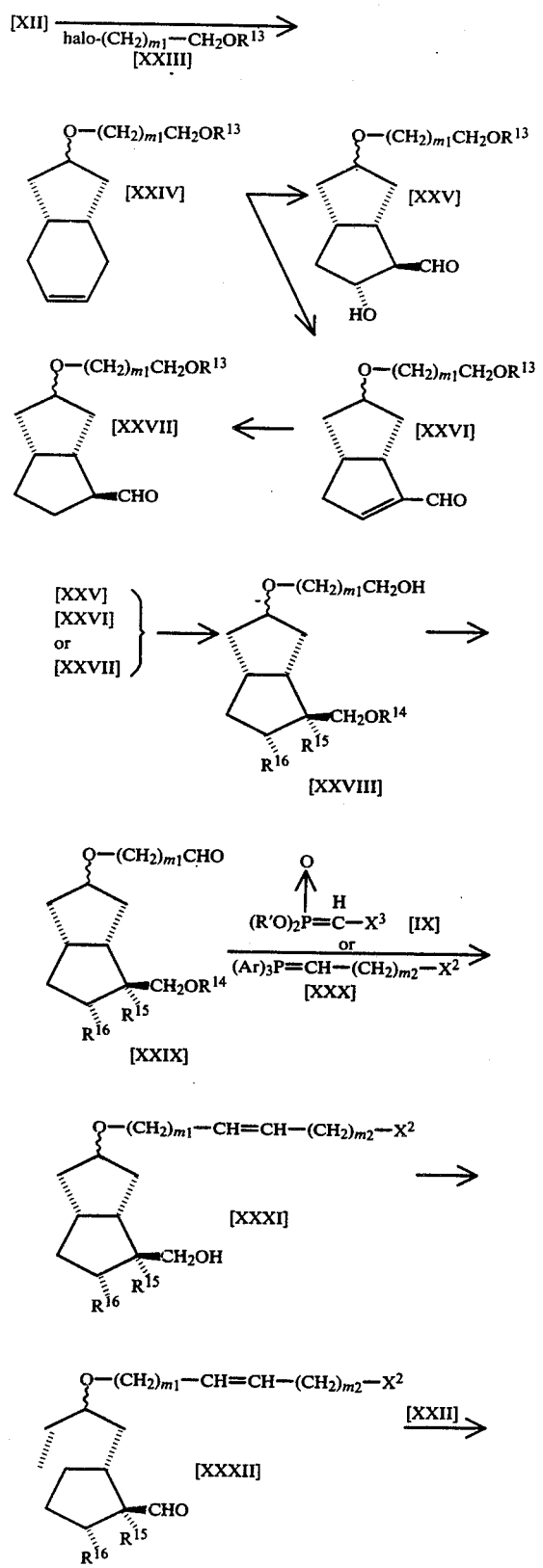
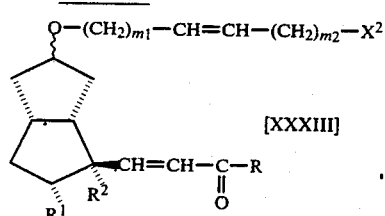
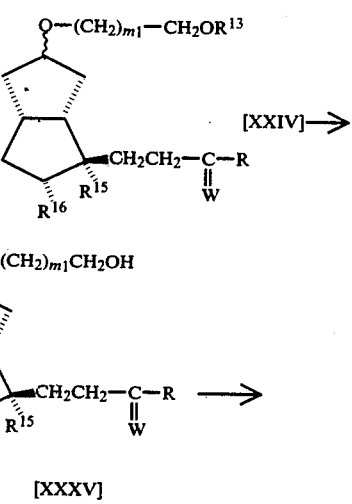
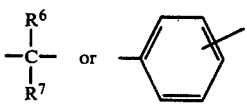
scheme E
In the formulae illustrated in the scheme C, D and E, A' is
halo[1] and halo[2] are a halogen atom, R is same as $R^4$ or $R^5$, R' is a $C_1$-$C_4$ alkyl group, Ar is an aryl group, $R^{13}$ and $R^{14}$ are a hydroxyl-protecting group, $R^{15}$ is a hydrogen atom, $R^{16}$ is a hydrogen atom or a protected hydroxyl group, or $R^{15}$ and $R^{16}$, when taken together, means a single linkage to form a double bond between the carbon-atoms to which they are linked, W is an oxygen atom or an ethylenedioxy group, and $m^1$, $m^2$, $R^1$, $R^2$, $R^4$, $R^5$, $X^2$ and $X^3$ are each as defined above.

Detailed explanation of Scheme C is as follows:

The compound [XII] is obtained from the ketone [XI] by metal hydride reduction. The compound [XIII] is obtained by reacting of the compound [XII] with the halide [XVI] followed by cyanation, optionally followed by hydrolysis of a cyano group and esterification of a carboxyl group. The reaction of the compound [XII] with the halide [XVI] can be carried out in an inert solvent (e.g. benzene, toluene, xylene, dimethylformamide, DMSO) at a range of the temperature from 50° C. to the boiling temperature of the solvent. Suitable condensation agents are alkali metal hydride (e.g. sodium hydride), alkali metal amide or alkali metal. The compound [XIII] can be also obtained by reacting the compound [XII] with the halide [XIV] in a similar manner as mentioned above. Oxidation of the compound [XIII] into the dialdehyde [XVII] can be accomplished by treating with sodium metaperiodate in the presence of a catalytic amount of osmium tetroxide in an inert solvent at a range of the temperature from 0° C. to room temperature. Example of the inert solvent include water, ethers (e.g. dioxane, THF) and aqueous ethers.

The aldehyde [XVII] can be also obtained by ozonization of the compound [XIII] at a range of the temperature from −80° C. to −30° C., followed by reductive cleavage with dialkyl sulfide, triphenylphosphine, sodium bisulfite, zinc or the like, or by the catalytic hydrogenation in the presence of a palladium on charcoal.

Examples of the inert solvent for ozonization include alkanols (e.g. methanol, ethanol), halogenated hydrocarbon and ether. Reduction of an ozonide may be accomplsihed by a per se conventional procedure at a range of the temperature from −30° C. to 0° C.

Aldol condensation of the dialdehyde [XVII] into an aldol derivative [XVIII] is carried out in the presence of an acid or a base in an inert solvent (e.g. water, alkanols, aqueous alkanols, ethers, esters) at a range of the temperature from −70° C. to room temperature. Examples of the suitable base are alkali hydroxide (e.g. potassium hydroxide, sodium hydroxide), alkali carbonate and alkali hydrogen carbonate.

The compound [XIX] can be obtained by treating the dialdehyde [XVII] in the presence of an acid or a base in an inert solvent at a range of the temperature from room temperature to the boiling temperature of the solvent.

The compound [XIX] can be easily converted into the compound [XX] by conventional catalytic hydrogenation in the presence of a palladium on charcoal, if necessary, followed by epimerization.

The compounds [XVIII, XIX, XX] can be each easily converted into a carbonyl compound [XXI] by reacting of the former with a compound [XXII] in an inert solvent (e.g. dioxane, ether, THF, dimethoxyethane, benzene, toluene, n-hexane, DMSO) at a range of the temperature from −10° C. to room temperature, optionally followed by protection of a hydroxyl group and/or reduction of a vinylene group.

Explanation of Scheme D is as follows:

The conversion from the compound [XII] into the aldehyde [XXV, XXVI, XXVII] can be conducted by a similar manner to the synthesis of the compounds [XVIII, XIX, XX]. The compound [XXV, XXVI, XXVII] can be easily converted through a compound [XXVIII] into the aldehyde [XXIX] by reduction of a formyl group, protection and deprotection of a hydroxyl group and oxidation of a hydroxyl group.

The compound [XXXI] can be obtained by wittig reaction of the compound [XXIX] with a compound [IX] or [XXX] and sequently deprotection of $R^{14}$ group, optionally followed by hydrolysis of an ester group.

The compound [XXXI] can be converted into a compound [XXXII] by reaction of the former with an oxidizing agent (e.g. Collin's reagent, Sarett reagent, pyridinium chlorochlomate) in an inert solvent (e.g. dichloromethane, dichloroethane, pyridine) at a range of the temperature from 0° C. to room temperature.

The compound [XXXIII] can be easily obtained from the compound [XXXII] by conventional wittig reaction with the compound [XXII], optionally followed by deprotection of a hydroxyl-protecting group.

Explanation of Scheme E is as follows:

The compound [XXV, XXVI, XXVII] can be converted into a compound [XXXIV] by reaction of the former with the compound [XXII], followed by protection of a hydroxyl group and reduction of a vinylene group, and, if necessary, followed by protection of a carbonyl group. The protection of a carbonyl group can be easily conducted by conventional procedure. The compound [XXXVII] can be obtained from the compound [XXXIV] by deprotection of a $R^{13}$ group, oxidation of a hydroxyl group and the wittig reaction with the compound [IX] or [XXX], optionally followed by deprotection of a carbonyl or hydroxyl group.

The alcohol compound [VII] used as an intermediate in the present invention can be prepared from the aldehyde compound [XXV, XXVI, XXVII] by reacting the latter with the compound of the formula

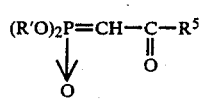  [XXXVIII]

wherein R' and $R^5$ are each as defined above to give a compound of the formula

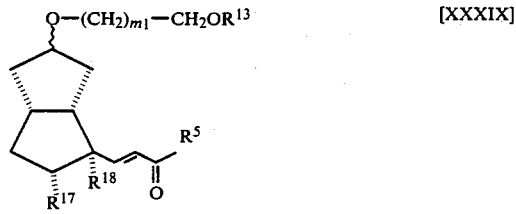  [XXXIX]

wherein $R^5$, $R^{13}$ and $m_1$ are each as defined above, $R^{17}$ is a hydrogen atom or a hydroxyl group, and $R^{18}$ is a hydrogen atom or $R^{17}$ and $R^{18}$ when taken together means a single linkage to form a double bond between the carbon atoms to which they are linked, followed by reacting the resulting compound with a reducing agent or an organometalic compound [IV], followed by protection of a hydroxy group and deprotection of a $R^{13}$ group, optionally followed by reduction of a vinylene group.

According to the present invention, the four stereoisomers of the formulae:

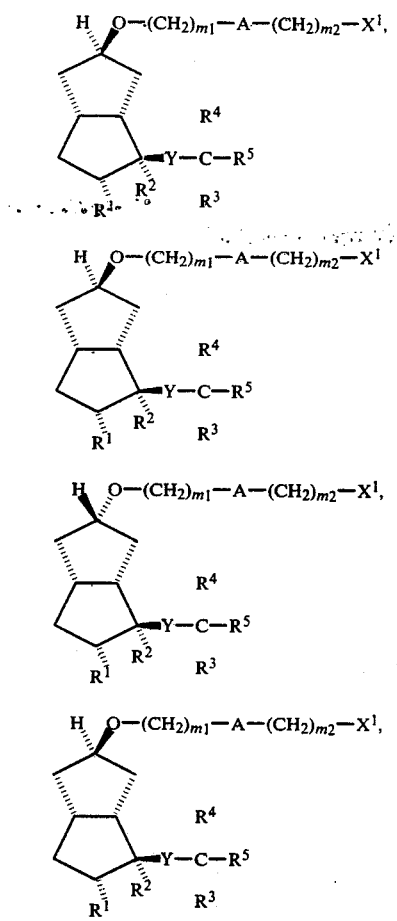

can be prepared. In general, the bicyclooctane compound [I] can be obtained as a mixture of these stereoisomers which can be easily separated by the conventional procedure with high purity.

If necessary, it is possible to yield selectively the bicyclooctane compound [I] of either one of these stereoisomers by changing the kinds and properties of solvents, reaction temperature, the organometalic compounds [IV, VI] and reducing agents.

It is also possible to convert the configuration of a hydroxy group of the compound [XII], by conventional procedures.

Among the bicyclooctane compounds [I] thus obtained, the compound [Ic] can be converted to its pharmacologically acceptable salt form. The pharmaceutically acceptable salts of these bicyclooctane compounds are those with pharmaceutically acceptable metal cation such as, sodium, potassium, magnesium and calcium, ammonium or amine cations.

And the compound [Ih] can be converted to the corresponding inorganic or organic acid addition salts by conventional procedures.

Bicyclooctane compounds [I] can be administered parenterally, orally to warm-blooded animals and human beings in the form of conventional pharmaceutical preparation.

For the preparation of pharmaceutical compositions containing at least one of the bicyclooctane compounds [I], they may be mixed with carriers, diluents, lubricants, fillers and/or binders such as lactose, sucrose, calcium, phosphate, starch, talcum, casein, magnesium stearate, methyl cellulose, polyglycols, tragacanth and the like, sometimes together with stabilizers and emulsifying agents. The resulting mixture may be processed in a usual manner to tablets, capsules, pills, ampoules and the like. The daily dosage may vary depending upon the administration route and the usual oral dosage of the active ingredient is between about 0.1 mg and about 20 mg daily for human beings.

Specific examples of the bicyclooctane compound [I] are as follows. Every compound below has four isomers, that is, (3'$\alpha$, 7$\alpha$), (3'$\alpha$, 7$\beta$), (3'$\beta$, 7$\alpha$) and (3'$\beta$, 7$\beta$).

2$\beta$-(3'-hydroxy-trans-1'-octenyl)3$\alpha$-hydroxy-7-(3"-carboxypropoxy)cis-bicyclo[3,3,0]octane

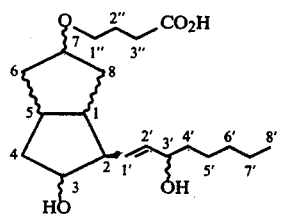

2$\beta$-(3'-hydroxy-3'-methyl-trans-1'-octenyl)3$\alpha$-hydroxy-7-(3"-carboxypropoxy)cis-bicyclo[3,3,0]octane 2$\beta$-(3'-hydroxy-4',4'-dimethyl-trans-1'-octenyl)3$\alpha$-hydroxy-7-(3"-carboxypropoxy)cis-bicyclo[3,3,0]octane 2$\beta$-(3'-hydroxy-5'-methyl-trans-1'-octenyl)3$\alpha$-hydroxy-7-(3"-carboxypropoxy)cis-bicyclo[3,3,0]octane 2$\beta$-(3'-hydroxy-5'-methyl-trans-1'-nonenyl)3$\alpha$-hydroxy-7-(3"-carboxypropoxy)cis-bicyclo[3,3,0]octane 2$\beta$-(3'-hydroxy-trans-1'-octenyl)3$\alpha$-hydroxy-7-(3"-methoxycarbonylpropoxy)cis-bicyclo[3,3,0]octane 2$\beta$-(3'-hydroxyoctyl)3$\alpha$-hydroxy-7-(3"-carboxypropoxy)cis-bicyclo[3,3,0]octane 2$\beta$(3'-hydroxy-3'-methyl-octyl)3$\alpha$-hydroxy-7-(3"-carboxypropoxy)cis-bicyclo[3,3,0]octane 2$\beta$-[4'-(p-fluorophenoxy)-3'-hydroxy-trans-1'-butenyl]3$\alpha$-hydroxy-7-(3"-carboxypropoxy)cis-bicyclo[3,3,0]octane 2$\beta$-(4'-phenoxy-3'-hydroxy-trans-1'-butenyl)-3$\alpha$-hydroxy-7-(3"-carboxypropoxy)cis-bicyclo[3,3,0]octane 2$\beta$-(4'-phenoxy-3'-hydroxy-butyl)-3$\alpha$-hydroxy-7-(3"-carboxypropoxy)cis-bicyclo[3,3,0]octane 2$\beta$-[4'-(p-chlorophenoxy)-3'-hydroxy-trans-1'-butenyl]-3$\alpha$-hydroxy-7-(3"-carboxypropoxy)cis-bicyclo[3,3,0]octane 2$\beta$-[4'-phenyl-3'-hydroxy-trans-1'-butenyl)-3$\alpha$-hydroxy-7-(3"-carboxypropoxy)cis-bicyclo[3,3,0]octane 2$\beta$-[4'-(m-trifluoromethylphenoxy)-3'-hydroxy-trans-1'-butenyl]-3$\alpha$-hydroxy-7-(3"-carboxypropoxy)cis-bicyclo[3,3,0]octane 2$\beta$-[4'-(p-fluorophenoxy)-3'-hydroxy-3'-methyl-trans-1'-butenyl]-3$\alpha$-hydroxy-7-(3"-carboxypropoxy)cis-bicyclo[3,3,0]octane 2$\beta$-[4'-(p-fluorophenoxy)-3'-hydroxybutyl]-3$\alpha$-hydroxy-7-(3"-carboxypropoxy)cis-bicyclo[3,3,0]octane 2β-[4'-(p-fluorophenoxy)-3'-hydroxy-trans-1'-butenyl]-3α-hydroxy-7-(3''-methoxycarbonylpropoxy)cis-bicyclo[3,3,0]octane 2β-[4'-(m-methylphenoxy)-3'-hydroxy-trans-1'-butenyl]-3α-hydroxy-7-(3''-carboxypropoxy)cis-bicyclo[3,3,0]octane 2β-[4'-(m-methxyphenoxy)-3'-hydroxy-trans-1'-butenyl]-3α-hydroxy-7-(3''-carboxypropoxy)cis-bicyclo[3,3,0]octane 2β-[4'-(p-methoxyphenoxy)-3'-hydroxy-trans-1'-butenyl]-3α-hydroxy-7-(3''-carboxypropoxy)cis-bicyclo[3,3,0]octane 2β-[4'-(p-fluorophenoxy)-3'-hydroxy-trans-1'-butenyl]-7-(3''-carboxypropoxy)-cis-bicyclo[3,3,0]octane 2β-[4'-(p-fluorophenoxy)-3'-hydroxybutyl]-7-(3''-carboxypropoxy)cis-bicyclo[3,3,0]octane 2β-(3'-hydroxyoctyl)-7-(3''-carboxypropoxy)cis-bicyclo[3,3,0]octane 2β-(3'-hydroxy-trans-1'-octenyl)-7-(3''-carboxypropoxy)cis-bicyclo[3,3,0]octane 2-(3'-hydroxy-trans-1'-octenyl)-7-(3''-carboxypropoxy)cis-bicyclo[3,3,0]oct-2-ene 2-(3'-hydroxy-4',4'-dimethyl-1'-trans-octenyl)-7-(3''-carboxypropoxy)cis-bicyclo[3,3,0]oct-2-ene 2-[4'-(p-fluorophenoxy)-3'-hydroxy-trans-1'-butenyl]-7-(3''-carboxypropoxy)cis-bicyclo[3,3,0]oct-2-ene 2β-[4'-(p-fluorophenoxy)-3'-hydroxy-trans-1'-butenyl]-3α-hydroxy-7-(3''-cyanopropoxy)cis-bicyclo[3,3,0]octane 2β-[4'-(p-fluorophenoxy)-3'-hydroxy-trans-1'-butenyl]-3α-hydroxy-7-(3''-aminocarbonylpropoxy)cis-bicyclo[3,3,0]octane 2β-[4'-(p-fluorophenoxy)-3'-hydroxy-trans-1'-butenyl]-3α-hydroxy-7-[3''-(dimethylaminocarbonyl)propoxy]cis-bicyclo[3,3,0]octane 2β-[4'-(p-fluorophenoxy)-3'-hydroxy-trans-1'-butenyl]-3α-hydroxy-7-(4''-hydroxybutoxy)cis-bicyclo-[3,3,0]octane 2β-[4'-(p-fluorophenoxy)-3'-hydroxy-trans-1'-butenyl]-3α-hydroxy-7-(4''-aminobutoxy)cis-bicyclo[3,3,0]octane 2β-[4'-(p-fluorophenoxy)-3'-hydroxy-trans-1'-butenyl]-3α-hydroxy-7-(4''-dimethylaminobutoxy)cis-bicyclo[3,3,0]octane 2β-[4'-(p-fluorophenoxy)-3'-hydroxy-trans-1'-butenyl]-3α-hydroxy-7-[3''-(piperidinocarbonyl)propoxy]cis-bicyclo[3,3,0]octane 2β-[4'-(p-fluorophenoxy)-3'-hydroxy-trans-1'-butenyl]-3α-hydroxy-7-[3''-(anilinocarbonyl)propoxy]cis-bicyclo[3,3,0]octane 2β-(3'-hydroxy-trans-1'-octenyl)3α-hydroxy-7-(3''-phenoxycarbonylpropoxy)cis-bicyclo[3,3,0]octane 2β-(3'-hydroxy-trans-1'-octenyl)3α-hydroxy-7-(3''-carboxy-trans-2''-propenoxy)cis-bicyclo[3,3,0]octane 2β-[4'-(p-fluorophenoxy)-3'-hydroxy-trans-1'-butenyl]3α-hydroxy-7-(3''-carboxy-trans-2''-propenoxy)cis-bicyclo[3,3,0]octane 2β-(3'-hydroxy-trans-1'-cis-5'-octadienyl)3α-hydroxy-7-(3''-carboxypropoxy)cis-bicyclo[3,3,0]octane 2β-(3'-hydroxy-trans-1'-propenyl)3α-hydroxy-7-(3''-carboxypropoxy)cis-bicyclo[3,3,0]octane 2β-(3'-hydroxy-4'-propoxy-trans-1'-butenyl)3α-hydroxy-7-(3''-carboxypropoxy)cis-bicyclo[3,3,0]octane 2β-(3'-hydroxy-trans-1'-octen-5'-ynl)3α-hydroxy-7-(3''-carboxypropoxy)cis-bicyclo[3,3,0]octane 2β-(3'-hydroxy-3'-cyclohexyl-trans-1'-propenyl)3α-hydroxy-7-(3''-carboxypropoxy)cis-bicyclo[3,3,0]octane 2β-(3'-hydroxy-trans-1'-octenyl)3α-hydroxy-7-(3''-carboxy-2'',2''-dimethylpropoxy)cis-bicyclo[3,3,0]octane 2β-(3'-hydroxy-trans-1'-octenyl)3α-hydroxy-7-(o-carboxybenzyloxy)cis-bicyclo[3,3,0]octane 2β-(3'-hydroxy-trans-1'-octenyl)3α-hydroxy-7-(m-carboxybenzyloxy)cis-bicyclo[3,3,0]octane 2β-(4'-cyclohexyl-3'-hydroxy-trans-1'-butenyl)-3α-hydroxy-7-(3''-carboxypropoxy)cis-bicyclo[3,3,0]octane 2β-(3'-hydroxy-trans-1'-octenyl)3α-hydroxy-7-(4''-anilinobutoxy)cis-bicyclo[3,3,0]octane 2β-(3'-hydroxy-trans-1'-octenyl)3α-hydroxy-7-(4''-piperidinobutoxy)cis-bicyclo[3,3,0]octane 2β-(3'-acetoxy-trans-1'-octenyl)3α-acetoxy-7-(3''-carboxypropoxy)cis-bicyclo[3,3,0]octane 2β-(3'-acetoxy-trans-1'-octenyl)3α-acetoxy-7-(3''-methoxycarbonylpropoxy)cis-bicyclo[3,3,0]octane 2β-(3'-acetoxy-trans-1'-octenyl)3α-hydroxy-7-(3''-carboxypropoxy)cis-bicyclo[3,3,0]octane 2β-(3'-benzoyloxy-trans-1'-octenyl)3α-benzoyloxy-7-(3''-carboxypropoxy)cis-bicyclo[3,3,0]octane Practical and preferred embodiments of the present invention are illustratively shown in the following examples, which are not intended to limit the scope of the invention thereto.

Preparative example (A) 5 g of sodium borohydride was added to a mixture of 9 g of 8-oxo-cis-bicyclo[4,3,0]non-3-ene and 60 ml of ethanol at room temperature while stirring, and the mixture was stirred for 30 minutes. The resulting mixture was poured into water and was extracted with ethyl acetate. The extract was washed with water, dried over anhydrous sodium sulfate and concentrated in vacuo to give 8-hydroxy-cis-bicyclo[4,3,0]non-3-ene NMR δ (CCl$_4$): 3.45(1H, d); 4.0–4.5; (1H, m); 5.65 (2H, s).

The compound obtained above was a mixture of two stereoisomers (8α, 8β) containing 8α as main product.

(B) 15 ml of a solution (THF) of tri-sec-butyllithium borohydride was added to a mixture of 1.36 g of 8-oxo-cis-bicyclo[4,3,0]non-3-ene and 60 ml of THF at −60° C.−−70° C. After stirring for a further 80 minutes at −60° C.−−70° C., an aqueous HCl was added and then the mixture was extracted with dichloromethane. The extract was washed with water, dried over anhydrous sodium sulfate and concentrated in vacuo. The residual oil was chromatographed on silica gel to give 8α-hydroxy-cis-bicyclo[4,3,0]non-3-ene.

NMR δ (CDCl$_3$) 4.18–4.48 (1H, m); 5.65; (2H, s).

(C) 1 ml of methanesulfonyl chloride was added to a mixture of 1 g of 8α-hydroxy-cis-bicyclo[4,3,0]non-3-ene, 4 ml of triethylamine and 10 ml of THF at 10° C.-20° C. After stirring a further 1 hr, the resulting mixture was poured into water and extracted with ethyl acetate. The extract was washed with water, dried over anhydrous sodium sulfate and concentrated in vacuo to give 8α-methanesulfonyloxy-cis-bicyclo[4,3,0]non-3-ene. 4.4 g of sodium acetate was added to a solution of 1.228 g of 8α-methanesulfonyloxy-cis-bicyclo[4,3,0]non-3-ene in 45 ml of dimethylformamide at room temperature. After stirring for 1 hr at 100° C.-110° C., the resulting mixture was poured into water and extracted with ethyl acetate. The extract was washed with water, dried over anhydrous sodium sulfate and concentrated in vacuo to give 8β-acetyloxy-cis-bicyclo[4,3,0]non-3-ene.

IR $\nu_{cm^{-1}}^{film}$ 1720

And then, a mixture of 0.86 g of 8β-acetyloxy-cis-bicyclo[4,3,0]non-3-ene, 6 ml of methanol, 3 ml of water and 0.3 g of potassium hydroxide was stirred for 1 hr at room temperature. The resulting mixture was poured into water and extracted with ethyl acetate. The extract was washed with water, dried over anhydrous sodium sulfate and concentrated in vacuo. The residual oil was chromatographed on silica gel to give 8β-hydroxy-cis-bicyclo[4,3,0]non-3-ene NMR δ (CCl$_4$) 4.2–4.5(1H, m); 5.62; (2H, s).

(D) 2.0 g of sodium hydride (50%) was added to a solution of 3.0 g of 8α-hydroxy-cis-bicyclo[4,3,0]non-3-ene in 100 ml of toluene at room temperature, and the mixture was refluxed for 30 minutes. After cooling, 2 g of 1-bromo-3-chloropropane was added to the resulting mixture at room temperature. After refluxing for 50 minutes, the reaction mixture was poured into water and extracted with ethyl acetate. The extract was washed with water, dried over anhydrous sodium sulfate and concentrated in vacuo to give an oil. 4.0 g of NaCN was added to a solution of this oil in 54 ml of DMSO at room temperature. After stirred for 30 minutes at 100° C.–120° C., 2.0 g of NaCN was added and the resulting mixture was stirred for a further 30 minutes at 100° C.–120° C.

The reaction mixture was poured into water and extracted with ether. The extract was washed with water, dried over anhydrous sodium sulfate, concentrated and distilled in vacuo to give 8α-(3'-cyanopropoxy)cis-bicyclo[4,3,0]non-3-ene.

B.P. 115°–120° C./1.0 mmHg (E) In the same manner as in (D), 8β-(3'-cyanopropoxy)cis-bicyclo[4,3,0]non-3-ene was obtained.

NMR δ (CCl$_4$) 3.43; (2H, t); 3.85–4.1 (1H, m); 5.65; (2H, s).

(F) Oxygen containing 3–4% of ozone was introduced into a solution of 1.0 g of 8α-(3'-cyanopropoxy)-cis-bicyclo[4,3,0]non-3-ene in 24 ml of methanol at −50° C. After stirring for 0.5 hr at −50°–60° C., 18 ml of dimethylsulfide was added into the resulting mixture at −20° C. After stirring for 2 hours at −5° C.—−20° C., the reaction mixture was concentrated by introduction of N$_2$ gas. The residue was dissolved in 20 ml of methanol and after cooling, 12 ml of 5% NaOHaq. was added into this solution at −10° C.—−15° C. After stirring for 25 minutes at −10° C.—−15° C., the resulting mixture was poured into water and extracted with ethyl acetate. The extract was washed with water, dried over anhydrous sodium sulfate and concentrated in vacuo to give 2β-formyl-3α-hydroxy-7α-(3'-cyanopropoxy)-cis-bicyclo[3,3,0]octane. To wittig reagent [formed from 0.39 g of sodium hydride, 1.52 g of dimethyl-2-oxo-heptylphosphonate and 66 ml of THF], a solution of the aldol obtained above in THF was added at 10°–25° C. After stirring for 30 minutes at room temperature, the resulting mixture was poured into water and extracted with ethyl acetate. The extract was washed with water, dried over anhydrous sodium sulfate, concentrated and chromatographed on silica gel to give 2β-(3'-oxo-trans-1'-octenyl)-3α-hydroxy-7α-(3''-cyanopropoxy)cis-bicyclo[3,3,0]octane.

NMR δ (CCl$_4$) 6.13; (1H, d); 6.73; (1H, d-d).

IR $\nu_{cm^{-1}}^{film}$ 2240, 1660, 1620.

(G) In the same manner as (F), the following compounds were obtained:

2β-[4'-(p-fluorophenoxy)-3'-oxo-trans-1'-butenyl]-3α-hydroxy-7-(3''-cyanopropoxy)cis-bicyclo[3,3,0]octane NMR δ (CDCl$_3$) 3.43 (2H, t); 4.68 (2H, s); 6.35 (1H, d).

2β-(4'-phenoxy-3'-oxo-trans-1'-butenyl)3α-hydroxy-7-(3''-cyanopropoxy)cis-bicyclo[3,3,0]octane NMR δ (CDCl$_3$) 3.45 (2H, t); 4.70 (2H, s); 6.43 (1H, d).

2β-(4'-phenyl-3'-oxo-trans-1'-butenyl)3α-hydroxy-7-(3''-cyanopropoxy)cis-bicyclo[3,3,0]octane NMR δ (CDCl$_3$) 3.46 (2H, t); 3.82 (2H, s); 6.20 (1H, d).

2β-[4'-(p-chlorophenoxy)-3'-oxo-trans-1'-butenyl]3α-hydroxy-7-(3''-cyanopropoxy)cis-bicyclo[3,3,0]octane NMR δ (CDCl$_3$) 3.44 (2H, t); 4.68 (2H, s); 6.40 (1H, d).

2β-(3'-oxo-trans-1'-octenyl)3α-hydroxy-7β-(3''-cyanopropoxy)cis-bicyclo[3,3,0]octane NMR δ (CCl$_4$) 6.07 (1H, d); 6.68 (1H, d-d).

2β-(3'-oxo-4',4'-dimethyl-trans-1'-octenyl)3α-hydroxy-7α-(3''-cyanopropoxy)cis-bicyclo-[3,3,0]octane NMR δ (CCl$_4$) 7.1–6.4 (2H, m), 3.7–4.0 (2H, m).

(H) 0.4 g of sodium hydride was added into a solution of 1 g of 8-hydroxy-cis-bicyclo[4,3,0]non-3-ene in 20 ml of toluene and the mixture was refluxed for 30 minutes. After cooling, 2 g of o-cyano-benzylbromide was added into the resulting mixture at 0° C.–10° C. After stirring for a further 3 hrs, at room temperature the reaction mixture was poured into water and extracted with ethyl acetate. The extract was washed with water, dried over anhydrous sodium sulfate and concentrated in vacuo. The residue was chromatographed on silica gel to give 8-(o-cyano-benzyloxy)cis-bicyclo[4,3,0]non-3-ene NMR δ (CCl$_4$) 4.57 (2H, s), 5.6 (2H, s).

(I) In the same manner as (F), 2β-(3'-oxo-trans-1'-octenyl)3α-hydroxy-7-(o-cyano-benzyloxy)cis-bicyclo[3,3,0]octane was obtained NMR δ (CCl$_4$) 4.6 (2H, s), 6.07 (1H, d), 6.68 (1H, dd).

(J) 1 g of the dialdehyde obtained in (F) as intermediate was dissolved in 20 ml of methanol and 0.2 g of potassium carbonate was added at room temperature. After stirring at room temperature, the resulting mixture was poured into water and extracted with ethyl acetate. The extract was washed with water, dried over anhydrous sodium sulfate and concentrated in vacuo to give 2-formyl-7α-(3'-cyanopropoxy)cis-bicyclo[3,3,0]oct-2-ene. From the aldehyde compound obtained above, 2-(3'-oxo-trans-1'-octenyl)-7α-(3''-cyanopropoxy)cis-bicyclo[3,3,0]-oct-2-ene was obtained in the same manner as (F).

NMR δ (CCl$_4$) 5.8–6.4 (2H, m), 7.2 (1H, d).

(K) In the same manner as (J), the following compound were obtained.

2-(3'-oxo-trans-1'-octenyl)-7β-(3''-cyanopropoxy)cis-bicyclo[3,3,0]oct-2-ene.

NMR δ (CCl$_4$) 5.87–6.1 (2H, m), 7.17 (1H, d).

2-(3'-oxo-4',4'-dimethyl-trans-1'-octenyl)-7α-(3''-cyanopropoxy)cis-bicyclo[3,3,0]oct-2-ene.

NMR δ (CCl$_4$) 5. (1H, br), 6.21 (1H, d), 7.21 (1H, d).

(L) 2.0 g of sodium hydride (50%) was added to a solution of 3.0 g of 8α-hydroxy-cis-bicyclo[4,3,0]non- 3-ene in 100 ml of toluene at room temperature, and the mixture was refluxed for 30 minutes. After cooling, 3.0 g of 1-chloro-2-tetrahydropyranyloxyethane added to the resulting mixture at room temperature.

After refluxing for 10 hrs, the reaction mixture was poured into water and extracted with ethyl acetate. The extract was washed with water, dried over anhydrous sodium sulfate and concentrated in vacuo to give an oil.

The oil thus obtained was dissolved in aqueous acetic acid [10 ml, acetic acid/water, 3/1 (V/V)] and stirred at 60° C. for 3 hrs. The reaction mixture was poured into water and extracted ethyl acetate. The extract was washed with aqueous sodium bicarbonate and water, dried over anhydrous sodium sulfate and concentrated in vacuo to give 8α-(2'-hydroxyethoxy)cis-bicyclo[4,3,0]non-3-ene.

The compound obtained above was treated with trityl chloride (3.0 g) in pyridine (20 ml). This mixture was heated for 1 hr at 100° C. and then concentrated in vacuo. The residue was diluted with ethyl acetate and washed with water. The organic layer was separated, dried over anhydrous sodium sulfate and concentrated to give the residue which was chromatographed over silica gel to yield 8α-(2'-trityloxyethoxy)cis-bicyclo[4,3,0]non-3-ene.

NMR δ (CDCl$_3$): 3.95–4.2 (1H, m) 5.66; (2H, s).

(M) In the same manner as (F), the following compound was obtained.

2β-(3'-oxo-trans-1'-octenyl)3α-hydroxy-7α-(2"-trityloxyethoxy)cis-bicyclo[3,3,0]octane.

NMR δ (CDCl$_3$): 3.55 (2H, t); 6.10 (1H, d); 6.70 (1H, d, d).

(N) To a methanolic solution of 0.8 g of 2β-(3'-oxo-trans-1'-octenyl)-3α-hydroxy-7α-(2"-trityloxyethoxy)-cis-bicyclo[3,3,0]octane was added 0.5 g of sodium borohydride in portions at −50°−−60° C. After stirring for 0.5 hr at the same temperature, the resulting mixture was poured into water and was extracted with ethyl acetate. The extract was washed with water, dried over anhydrous sodium sulfate and concentrated in vacuo to give 2β-(3'-hydroxy-trans-1'-octenyl)-3α-hydroxy-7α-(2"-trityloxyethoxy)cis-bicyclo[3,3,0]octane.

The diol obtained above was treated with acetic anhydride (2 ml) and pyridine (3 ml). After stirring for 17 hrs at room temperature, the reaction mixture was extracted with ethyl acetate. The extract was washed with water, dried over anhyrous sodium sulfate and concentrated in vacuo to give 2β-(3'-acetoxy-trans-1'-octenyl)-3α-acetoxy-7α-(2"-trityloxyethoxy)cis-bicyclo[3,3,0]octane.

The compound obtained above was dissolved in aqueous acetic acid (5 ml, acetic acid/water, 4/1), and the mixture was heated at 100°–110° C. for 0.5 hr.

After diluted with water, the mixture was extracted with ethyl acetate, the extract was washed with aqueous sodium bicarbonate and water, dried over anhydrous sodium sulfate and concentrated in vacuo. The residue was chromatographed on silica gel to give 2β-(3'-acetoxy-trans-1'-octenyl)3α-acetoxy-7α-(2"-hydroxyethoxy)cis-bicyclo[3,3,0]octane.

NMR δ (CDCl$_3$): 2.03 (3H, s); 2.06 (3H, s); 3.53 (2H, m).

(O) A mixture of 1.0 g of 8α-(3'-cyanopropoxy)cis-bicyclo[4,3,0]non-3-ene, 2.0 g of potassium hydroxide, 8 g of water and 20 ml of ethanol was reflux for 2.5 hrs. After cooling, the resulting mixture was poured into water and washed with ether. The aqueous layer was acidified and extracted with ethyl acetate. The organic layer was washed with water, dried over anhydrous sodium sulfate and concentrated in vacuo. The residue was dissolved in ether and an ether solution of diazomethane was added to this solution at room temperature. After standing at room temperature for 1 hr, the resulting mixture was concentrated in vacuo to give 8α-(3'-methoxycarbonylpropoxy)cis-bicyclo[4,3,0]non-3-ene.

NMR δ (CDCl$_3$): 3.63 (3H, s); 5.65 (2H, s).

(P) In the same mannner as (F), the following compound was obtained.

2β-(3'-oxo-trans-1'-octenyl)3α-hydroxy-7α-(3"-methoxycarbonylpropoxy)cis-bicyclo[3,3,0]octane.

NMR δ (CDCl$_3$): 3.63 (2H, s); 6.08 (1H, d); 6.69 (1H, d, d).

Example-1

0.38 g of sodium borohydride was added in' portions into a solution of 0.38 g of 2β-(3'-oxo-trans-1'-octenyl)-3α-hydroxy-7α-(3"-cyanopropoxy)cis-bicyclo[3,3,0]octane in 10 ml of methanol at −50°−−60° C. After stirring for 1 hour at −40°−−50° C., the resulting mixture was poured into water and extracted with ethyl acetate. The extract was washed with water, dried over anhydrous sodium sulfate and concentrated in vacuo. The residue was chromatographed on silica gel to give 2β-(3'β-hydroxy-trans-1'-octenyl)-3α-hydroxy-7α-(3"-cyanopropoxy)cis-bicyclo[3,3,0]octane NMR δ (CDCl$_3$) 3.48 (2H, t), 3.6–4.2 (3H, m) 5.47–5.6 (2H, m), and 2β-(3'α-hydroxy-trans-1'-octenyl)3α-hydroxy-7α-(3"-cyanopropoxy)cis-bicyclo[3,3,0]octane NMR δ (CDCl$_3$) 3.48 (2H, t), 3.7–4.3 (3H, m); 5.5–5.77 (2H, m).

Example-2

In the same manner as in example-1, the following compound were obtained.

2β-(3'β-hydroxy-trans-1'-octenyl)3α-hydroxy-7β-(3"-cyanopropoxy)cis-bicyclo[3,3,0]octane NMR δ (CDCl$_3$) 3.49 (2H, t), 3.6–4.3 (3H, m), 5.55–5.65 (2H, m).

2β-(3'α-hydroxy-trans-1'-octenyl)3α-hydroxy-7β-(3"-cyanopropoxy)cis-bicyclo[3,3,0]octane NMR δ (CDCl$_3$) 3.48 (2H, t), 3.6–4.2 (3H, m), 5.45–5.6 (2H, m).

2β-[4'-(p-fluorophenoxy)-3'-hydroxy-trans-1'-butenyl]3α-hydroxy-7-(3"-cyanopropoxy)cis-bicyclo[3,3,0]octane NMR δ (CDCl$_3$) 3.47 (2H, t), 5.53–5.8 (2H, br).

2β-(4'-phenoxy-3'-hydroxy-trans-1'-butenyl)3α-hydroxy-7-(3"-cyanopropoxy)cis-bicyclo[3,3,0]octane NMR δ (CDCl$_3$) 3.48 (2H, t); 5.6–5.87 (2H, br).

2β-(4'-phenyl-3'-hydroxy-trans-1'-butenyl)3α-hydroxy-7-(3"-cyanopropoxy)cis-bicyclo[3,3,0]octane NMR δ (CDCl$_3$) 3.47 (2H, t), 5.33–5.63 (2H, br).

2β-[4'-(p-chlorophenoxy)-3'-hydroxy-trans-1'-butenyl]3α-hydroxy-7-(3"-cyanopropoxy)cis-bicyclo[3,3,0]octane NMR δ (CDCl$_3$) 3.45 (2H, t), 5.5–5.9 (2H, br).

2β-(3'α-hydroxy-4',4'-dimethyl-trans-1'-octenyl)3α-hydroxy-7α-(3"-cyanopropoxy)cis-bicyclo[3,3,0]octane NMR δ (CDCl$_3$); 5.4–5.8 (2H, m), 3.3–4.2 (5H, m)

2β-(3'-hydroxy-trans-1'-octenyl)3α-hydroxy-7-(o-cyanobenzyloxy)cis-bicyclo[3,3,0]octane NMR δ (CDCl$_3$) 4.65 (2H, s), 5.3–5.8 (2H, br), 7.2–7.8 (4H, m).

2β-(3'β-hydroxy-4',4'-dimethyl-trans-1'-octenyl)3α-hydroxy-7α-(3''-cyanopropoxy)cis-bicyclo[3,3,-0]octane NMR δ (CDCl$_3$); 3.5 (2H, t-like), 5.5–5.8 (2H, br).

2-(3'-hydroxy-trans-1'-octenyl)-7α-(3''-cyanopropoxy)cis-bicyclo[3,3,0]oct-2-ene NMR δ (CCl$_4$); 5.3–5.7 (2H, m), 6.27 (1H, d).

2-(3'-hydroxy-trans-1'-octenyl)-7β-(3''-cyanopropoxy)-cis-bicyclo[3,3,0]oct-2-ene NMR δ (CDCl$_3$), 5.4–5.7 (2H, m), 6.33 (1H, d).

2-(3'-hydroxy-4',4'-dimethyl-trans-1'-octenyl)7α-(3''-cyanopropoxy)cis-bicyclo[3,3,0]oct-2-ene NMR δ (CDCl$_3$); 5.47–5.77 (2H, m), 6.38 (1H, d).

Example-3

A mixture of 100 mg of 2β-[4'-(p-fluorophenoxy)3'-hydroxy-trans-1'-butenyl]3α-hydroxy-7-(3''-cyanopropoxy)-cis-bicyclo[3,3,0]octane, 0.2 g of potassium hydroxide, 0.8 g of water and 2 g of ethanol was refluxed for 2.5 hours. After cooling, the resulting mixture was poured into water and washed with ether. The aqueous layer was acidified and extracted with ethyl acetate. The organic layer was washed with water, dried over anhydrous sodium sulfate and concentrated in vacuo. The residue was chromatographed on silica gel to give 2β-[4'-(p-fluorophenoxy)-3'-hydroxy-trans-1'-butenyl]3α-hydroxy-7-(3''-carboxypropoxy)cis-bicyclo[3,3,0]octane NMR δ (CDCl$_3$) 3.36 (2H, t), 4.2–4.6 (1H, br).
IR ν$^{film}_{cm-1}$ 1700.

Example-4

In the same manner as in Example-3, the following compounds were obtained:

2β-(4'-phenoxy-3'-hydroxy-trans-1'-butenyl)3α-hydroxy-7-(3''-carboxypropoxy)cis-bicyclo[3,3,-0]octane NMR δ (CDCl$_3$) 3.35 (2H, t) 4.2–4.6 (1H, br).
IR ν$^{film}_{cm-1}$ 1700–1710.

2β-[4'-(p-chlorophenoxy)-3'-hydroxy-trans-1'-butenyl]3α-hydroxy-7-(3''-carboxypropoxy)cis-bicyclo[3,3,0]octane NMR δ (CDCl$_3$) 3.35 (2H, t), 4.2–4.6 (1H, br).
IR ν$^{film}_{cm-1}$ 1700.

2β-(4'-phenyl-3'-hydroxy-trans-1'-butenyl)3α-hydroxy-7-(3''-carboxypropoxy)cis-bicyclo[3,3,-0]octane NMR δ (CDCl$_3$) 3.37 (2H, t); 2.8 (2H, d); 4.03–4.37 (1H, br).
IR ν$^{film}_{cm-1}$ 1680–1720.

2β-(3'α-hydroxy-trans-1'-octenyl)3α-hydroxy-7α-(3''-carboxypropoxy)cis-bicyclo[3,3,0]octane NMR δ (CDCl$_3$) 5.53–5.76 (2H, m).

2β-(3'β-hydroxy-trans-1'-octenyl)3α-hydroxy-7α-(3''-carboxypropoxy)cis-bicyclo[3,3,0]octane NMR δ (CDCl$_3$) 5.35–5.58 (2H, m) 3.4 (2H, t).

2β-(3'α-hydroxy-trans-1'-octenyl)3α-hydroxy-7β-(3''-carboxypropoxy)cis-bicyclo[3,3,0]octane NMR δ (CDCl$_3$) 5.53–5.67 (2H, m); 3.47 (2H, t).

2β-(3'β-hydroxy-trans-1'-octenyl)3α-hydroxy-7β-(3''-carboxypropoxy)cis-bicyclo[3,3,0]octane NMR δ (CDCl$_3$) 5.53–5.67 (2H, m); 3.45 (2H, t).

2β-(3'α-hydroxy-4',4'-dimethyl-trans-1'-octenyl)3α-hydroxy-7α-(3''-carboxypropoxy)cis-bicyclo[3,3,-0]octane NMR δ (CDCl$_3$); 0.7–1.0 (9H, d-like), 3.3–4.2 (5H, m).

2β-(3'β-hydroxy-4',4'-dimethyl-trans-1'-octenyl)3α-hydroxy-7α-(3''-carboxypropoxy)cis-bicyclo[3,3,-0]octane NMR δ (CDCl$_3$); 0.7–1.1 (9H, m), 3.2–4.1 (5H, m).

2β-(3'-hydroxy-trans-1'-octenyl)3α-hydroxy-7-(o-carboxybenzyloxy)cis-bicyclo[3,3,0]octane NMR δ (CDCl$_3$); 5.4–5.73 (2H, br).

2-(3'-hydroxy-4',4'-dimethyl-trans-1'-octenyl)-7α-(3''-carboxypropoxy)cis-bicyclo[3,3,0]oct-2-ene IR ν$^{film}_{cm-1}$ 1705.

Example-5

To a solution of 100 mg of 2β-(3'α-hydroxy-trans-1'-octenyl)3α-hydroxy-7α-(3''-carboxypropoxy)cis-bicyclo[3,3,0]octane in 10 ml of THF, an ether solution of diazomethane was added at room temperature. After stirring at room temperature, the resulting mixture was concentrated in vacuo to give 2β-(3'α-hydroxy-trans-1'-octenyl)3α-hydroxy-7α-(3''-methoxy carbonylpropoxy)cis-bicyclo[3,3,0]octane NMR (CDCl$_3$) 5.4–5.8 (2H, m).
IR ν$^{film}_{cm-1}$ 1720.

Example-6

In the same manner as in Example-5, the following compound was obtained.

2β-[4'-(p-fluorophenoxy)-3'-hydroxy-1'-trans-butenyl]3α-hydroxy-7-(3''-methoxycarbonylpropoxy)cis-bicyclo[3,3,0]octane NMR δ (CDCl$_3$) 3.35 (2H, t).
IR ν$^{film}_{cm-1}$ 1720.

Example-7

A mixture of 40 mg of 2β-[4'-(p-fluorophenoxy)-3'-hydroxy-trans-1'-butenyl]3α-hydroxy-7-(3''-carboxypropoxy)cis-bicyclo[3,3,0]octane, 20 mg of 10% palladium on charcoal and 10 ml of ethanol was vigorously stirred under atmospheric hydrogen at room temperature until an equimolar amount of hydrogen was consumed. The catalyst was filtered off, and the filtrate was concentrated in vacuo to give 2β-[4'-(p-fluorophenoxy)-3'-hydroxybutyl]3α-hydroxy-7-(3''-carboxypropoxy)cis-bicyclo[3,3,0]octane NMR δ (CDCl$_3$) 3.42 (2H, t); 5.1–5.5 (3H, br).

Example-8

To a stirred mixture of 100 mg of lithium aluminium hydride and 5 ml of ether, was added dropwise a solution of 50 mg of 2β-(4'-phenoxy-3'-hydroxy-trans-1'-butenyl)3α-hydroxy-7-(3''-carboxypropoxy)cis-bicyclo[3,3,0]octane in 5 ml of THF at room temperature. After refluxing for 30 min, a mixture of 1 ml of water and 5 ml of THF was added to the reaction mixture under cooling with ice. The resulting mixture was poured into water and extracted with ethyl acetate. The extract was washed with water, dried over anhydrous sodium sulfate and concentrated in vacuo. The residue was chromatographed on silica gel to give 2β-(4'-phenoxy-3'-hydroxy-trans-1'-butenyl)3α-hydroxy-7-(4''-hydroxy-butoxy)cis-bicyclo[3,3,0]octane.

NMR δ (CDCl$_3$) 5.4–5.85 (2H, m)

Example-9

To a solution of 50 mg of 2β-(3'-hydroxy-4'-phenoxy-trans-1'-butenyl)3α-hydroxy-7-(3"-carboxypropoxy)cis-bicyclo[3,3,0]octane in 3 ml of THF, 24 mg of ethylchloroformate was added at 0° C., and sequently was added 48.5 mg of triethylamine at 0° C. After stirring for 20 min at 0° C., 20 mg of piperidine was added at 0° C. and stirred for a further 1 hr. The reaction mixture was stirred for 10 hours, and then poured into water and extracted with ethyl acetate. The extracted was washed with water, dried over anhydrous sodium sulfate and concentrated in vacuo. The residue was chromatographed on silica gel to give 2β-(3'-hydroxy-4'-phenoxy-trans-1'-butenyl)3α-hydroxy-7-[3"-(piperidinocarbonyl)propoxy]cis-bicyclo[3,3,0]octane.

IR $\nu_{cm^{-1}}^{film}$ 1650,

NMR δ (CDCl$_3$); 5.6–5.8 (2H, m); 6.8–7.45 (5H, m).

Example-10

In the same manner as in Example-9, 2β-(3'-hydroxy-4'-phenyl-trans-1'-butenyl)3α-hydroxy-7-(3"-dimethylaminocarbonylpropoxy)cis-bicyclo[3,3,0]octane was obtained.

IR $\nu_{cm^{-1}}^{film}$ 1650,

NMR δ (CDCl$_3$); 7.0–7.3 (5H, s).

Example-11

To a stirred mixture of 100 mg of lithium aluminium hydride and 5 ml of ether, was added dropwise a solution of 50 mg of 2β-(3'α-hydroxy-trans-1'-octenyl)3α-hydroxy-7α-(3"-cyanopropoxy)cis-bicyclo[3,3,0]octane in 5 ml of THF at room temperature. After refluxing for 1 hr, 5 ml of water was added, and the resulting mixture was poured into water and extracted with ethyl acetate. The extract was washed with water, dried over anhydrous sodium sulfate and concentrated in vacuo. The residue was chromatographed on silica gel to give 2β-(3'α-hydroxy-trans-1'-octenyl)3α-hydroxy-7α-(4"-amino-butoxy)cis-bicyclo[3,3,0]octane NMR δ (CDCl$_3$); 5.5–5.8 (2H, m).

Example-12

To a suspension of pyridinium chlorochromate (0.6 g) in dry dichloromethane (5 ml) was added a solution of 0.5 g of 2β-(3'-acetoxy-trans-1'-octenyl)3α-acetoxy-7α-(2"-hydroxyethoxy)cis-bicyclo[3,3,0]octane in dichloromethane at room temperature under nitrogen. After 1 hr, ether was added. The mixture was filtered and washed with ether. The filtrate was concentrated in vacuo to give 2β-(3'-acetoxy-trans-1'-octenyl)3α-acetoxy-7α-formylmethoxy-cis-bicyclo[3,3,0]octane.

The aldehyde thus obtained was treated with a tetrahydrofuran solution of the yield prepared from diethyl ethoxycarbonylmethyl phosphonate (0.45 g) and sodium hydride (50%, 0.1 g) and THF (10 ml).

After stirring for 2 hrs at room temperature, the resulting mixture was poured into water and extracted with ethyl acetate. The extract was washed with water, dried over anhydrous sodium sulfate and concentrated in vacuo. The residue was chromatographed on silica gel to give 2β-(3'-acetoxy-trans-1'-octenyl)3α-acetoxy-7α-(3"-ethoxycarbonyl-trans-2"-propenoxy)cis-bicyclo[3,3,0]octane.

NMR δ (CDCl$_3$): 1.25 (3H, t), 2.03 (3H, s), 2.07 (3H, s).

Example-13

Into a solution of 0.3 g of 2β-(3'-oxo-trans-1'-octenyl)3α-hydroxy-7α-(3"-methoxycarbonyl propoxy)cis-bicyclo[3,3,0]octane in dry ether was added a solution of methylmagnesium iodide (2 eq) in dry ether at −10°–0° C. After stirring at same temperature for 2 hrs, the mixture was poured into saturated ammonium chloride solution and extracted with ethyl acetate. The extract was washed with aqueous sodium bicarbonate, dried over anhydrous sodium sulfate, and concentrated in vacuo.

The residue was chromatographed on silica gel to give 2β-(3'-hydroxy-3'-methyl-trans-1'-octenyl)3α-hydroxy-7α-(3"-methoxycarbonylpropoxy)cis-bicyclo[3,3,0]octane.

NMR δ (CDCl$_3$): 1.25 (3H, s), 3.63 (3H, s).

Example-14

In the same manner as in Example-3, the following compounds were obtained.

2β-(3'-hydroxy-trans-1'-octenyl)3α-hydroxy-7α-(3"-carboxy-trans-2"-propenoxy)cis-bicyclo[3,3,0]octane.

NMR δ (CDCl$_3$): 5.4–5.6 (2H, m); 6.0 (1H, d); 6.8–7.2 (1H, m).

2β-(3'-hydroxy-3'-methyl-trans-1'-octenyl)3α-hydroxy-7α-(3"-carboxypropoxy)cis-bicyclo[3,3,0]octane.

NMR δ (CDCl$_3$): 1.25 (3H, s); 5.4–5.6 (2H, m).

What is claimed is:

1. A compound of the formula

[Structure: bicyclic compound with substituents O—(CH$_2$)$_{m1}$—A—(CH$_2$)$_{m2}$—X$^1$ and side chain Y—C(R$^4$)(R$^5$)(R$^3$), with R$^1$, R$^2$ on the ring]

wherein

X$^1$ is COOH, C$_1$–C$_4$ alkoxycarbonyl, phenoxycarbonyl, phenylalkyloxycarbonyl, (C$_1$–C$_4$ alkoxy)methoxycarbonyl, (C$_2$–C$_5$ alkanoyloxy)methoxycarbonyl, (C$_3$–C$_7$ cycloalkyloxy)carbonyl, phenylcarbonylmethoxycarbonyl, or (hydroxy C$_1$–C$_4$ alkoxy)carbonyl, Y is ethylene or vinylene, R$^1$ is —H, —OH, —OC$_1$–C$_4$alkanoyl, —O—benzoyl, or —O—(C$_1$–C$_4$ alkoxy)alkyl, R$^2$ is H or R$^1$ or R$^2$, when taken together, are a single linkage forming a double bond between the carbon atoms to which they are linked, R$^3$ is OH, —OC$_1$–C$_4$ alkanoyl, —O—benzoyl, or —O(C$_1$–C$_4$ alkoxy)alkyl, R$^4$ is H or C$_1$–C$_4$ alkyl, R$^5$ is H, C$_3$–C$_8$ alkenyl, C$_3$–C$_8$ alkynyl, C$_1$–C$_8$ alkyl, C$_3$–C$_7$ cycloalkyl or a group of the formula —(CH$_2$)$_n$—B where n is 1 or 2 and B is C$_1$–C$_4$ alkoxy, C$_3$–C$_7$ cycloalkyl, phenyl, phenoxy, phenyl substituted with any of a halogen atom, C$_1$–C$_4$ alkyl, CF$_3$, or C$_1$–C$_4$ alkoxy; or phenoxy substituted with any of a halogen atom, C$_1$–C$_4$ alkyl, CF$_3$, or C$_1$–C$_4$ alkoxy;

A is

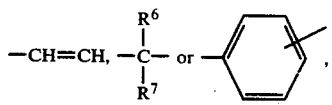

wherein $R^6$ and $R^7$ are each independently H or $C_1$–$C_4$ alkyl;
$m_1$ is 1 or 2, and
$m_2$ is 0, 1 or 2, and an effective, anti-ulcerogenic non-toxic pharmaceutically acceptable salt thereof.

2. A compound of the formula

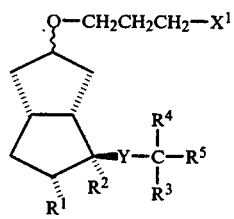

wherein $X^1$, Y, $R^1$, $R^2$, $R^3$, $R^4$ and $R^5$ are each as defined in claim 1, and their non-toxic pharmaceutically acceptable salts thereof.

3. A compound of the formula

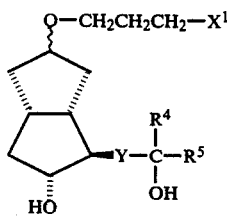

wherein $X^1$, Y, $R^4$ and $R^5$ are each as defined in claim 1.

4. The compound according to claim 3, wherein Y is a vinylene group.

5. The compound according to claim 3, wherein $R^5$ is a $C_1$–$C_8$ alkyl group.

6. The compound according to claim 3, wherein $R^5$ is a group of the formula: —CH$_2$—D—G, wherein D is an oxygen atom or a single bond, and G is a phenyl group optionally substituted with halogen, $C_1$–$C_4$ alkyl or trifluoromethyl.

7. 2β-(3'α-hydroxy-trans-1'-octenyl)-3α-hydroxy-7α-(3''-carboxypropoxy)cis-bicyclo[3,3,0]octane, and its stereoisomers (3'β and/or 7β).

8. 2β-(3'α-hydroxy-trans-1'-octenyl)-3α-hydroxy-7α-(o-carboxybenzyloxy)cis-bicyclo[3,3,0]octane, and its stereoisomers (3'β and/or 7β).

9. 2β-(3'α-hydroxy-4',4'-dimethyl-trans-1'-octenyl)-3α-hydroxy-7α-(3''-carboxypropoxy)cis-bicyclo[3,3,0]octane, and its stereoisomers (3'β and/or 7β).

10. 2β-(3'α-hydroxy-3'β-methyl-trans-1'-octenyl)-3α-hydroxy-7α-(3''-carboxypropoxy)cis-bicyclo[3,3,0]octane, and its stereoisomers (3'β and/or 7β).

11. 2β-(3'α-hydroxy-octyl)-3α-hydroxy-7α-(3''-carboxypropoxy)cis-bicyclo[3,3,0]octane, and its stereoisomers (3'β and/or 7β).

12. 2β-[4'-(p-fluorophenoxy)-3'α-hydroxy-trans-1'-butenyl]-3α-hydroxy-7α-(3''-carboxypropoxy)cis-bicyclo[3,3,0]octane, and its stereoisomers (3'β and/or 7β).

13. 2β-[4'-(p-fluorophenoxy)-3'α-hydroxy-butyl]-3α-hydroxy-7α-(3''-carboxypropoxy)cis-bicyclo[3,3,0]octane, and its stereoisomers (3'β and/or 7β).

14. 2β-(4'-phenoxy-3'α-hydroxy-trans-1'-butenyl)-3α-hydroxy-7α-(3''-carboxypropoxy)cis-bicyclo[3,3,0]octane, and its stereoisomers (3'β and/or 7β).

15. 2β-(4'-phenyl-3'α-hydroxy-1'-butenyl)-3α-hydroxy-7α-(3''-carboxypropoxy)cis-bicyclo[3,3,0]octane, and its stereoisomers (3'β and/or 7β).

16. 2β-(3'α-hydroxy-trans-1'-octenyl)-3α-hydroxy-7α-(3''-carboxy-trans-2''-propenoxy)cis-bicyclo[3,3,0]octane, and its stereoisomers (3'β and/or 7β).

17. A pharmaceutically acceptable salt of a compound as claimed in claim 1, wherein $X^1$ is a carboxyl group.

18. The compound according to claim 4, wherein $X^1$ is COOH, $C_1$–$C_4$ alkoxycarbonyl, phenoxycarbonyl, phenylalkyloxycarbonyl, ($C_1$–$C_4$ alkoxy)methoxycarbonyl, ($C_2$–$C_5$ alkanoyloxy)methoxycarbonyl, ($C_3$–$C_7$ cycloalkyloxy)carbonyl, phenylcarbonylmethoxycarbonyl, or (hydroxy $C_1$–$C_4$ alkoxy)carbonyl, and $R^5$ is a $C_1$–$C_8$ alkyl group.

19. The compound according to claim 4, wherein $X^1$ is COOH, $C_1$–$C_4$ alkoxycarbonyl, phenoxycarbonyl, phenylalkyloxycarbonyl, ($C_1$–$C_4$ alkoxy)methoxycarbonyl, ($C_2$–$C_5$ alkanoyloxy)methoxycarbonyl, ($C_3$–$C_7$ cycloalkyloxy)carbonyl, phenylcarbonylmethoxycarbonyl, or (hydroxy $C_1$–$C_4$ alkoxy)carbonyl, and $R^5$ is a group of the formula —CH$_2$—D—G where D is an oxygen atom or a single bond, and G is a phenyl group optionally substituted with halogen, $C_1$–$C_4$ alkyl, trifluoromethyl, or $C_1$–$C_4$ alkoxyl.

20. A pharmaceutical composition for the treatment of ulcers comprising
an anti-ulcerogenic effective amount of a compound of claim 1 and
a pharmaceutically acceptable carrier or diluent.

* * * * *